United States Patent [19]

Hudgin et al.

[11] 3,975,350

[45] *Aug. 17, 1976

[54] HYDROPHILIC OR HYDROGEL CARRIER SYSTEMS SUCH AS COATINGS, BODY IMPLANTS AND OTHER ARTICLES

[75] Inventors: Donald Edward Hudgin, Princeton Junction; Edgar Allan Blair, Cranbury, both of N.J.

[73] Assignee: Princeton Polymer Laboratories, Incorporated, Plainsboro, N.J.

[ * ] Notice: The portion of the term of this patent subsequent to July 2, 1991, has been disclaimed.

[22] Filed: June 25, 1974

[21] Appl. No.: 482,874

Related U.S. Application Data

[63] Continuation-in-part of Ser. No. 277,361, Aug. 2, 1972, Pat. No. 3,822,238.

[52] U.S. Cl. ................................ 260/30.4 N; 3/1; 3/1.4; 3/1.5; 3/1.91; 128/348; 128/350 R; 128/127; 128/334 R; 260/2.5 AD; 260/2.5 A; 260/32.6 N; 260/75 NK; 260/77.5 AP; 260/77.5 AQ; 260/75 NQ; 260/77.5 AS; 260/77.5 AR; 260/2 EN; 424/78; 424/81; 428/425

[51] Int. Cl.$^2$ ................ C08G 18/48; C08G 18/30; C08G 18/32; A61F 1/00

[58] Field of Search.. 260/2.5 AD, 75 NK, 77.5 AP, 260/2.5 A, 30.4 N, 32.6 N, 77.5 AQ; 239/6, 57; 3/1, 1.4; 424/78

[56] References Cited

UNITED STATES PATENTS

| | | | |
|---|---|---|---|
| 1,968,136 | 7/1934 | Gardner | 239/6 |
| 3,129,888 | 4/1964 | O'Hagan | 239/57 |
| 3,247,841 | 4/1966 | Cook | 260/2.5 A |
| 3,497,990 | 3/1970 | Jeffries | 239/57 |
| 3,536,260 | 10/1970 | Volz | 239/6 |
| 3,627,735 | 12/1971 | Trapasso | 260/77.5 SP |
| 3,706,678 | 12/1972 | Dietrich et al. | 260/2.5 AT |
| 3,806,474 | 4/1974 | Blair | 260/2.5 AN |
| 3,819,405 | 6/1974 | Engle | 239/6 |
| 3,822,238 | 7/1974 | Blair et al. | 260/75 NK |
| 3,939,123 | 2/1976 | Matthews et al. | 260/77.5 AM |

*Primary Examiner*—H.S. Cockeram
*Attorney, Agent, or Firm*—Curtis, Morris & Safford

[57] ABSTRACT

Improved active agent systems with novel carriers as membrane, release, and coating polymers for said active agents; the polymers are water absorptive polyurethane polymers prepared from resins having a low ratio of carbon to oxygen to nitrogen or having ionic, quaternary ammonium or salt groups in the resin backbone and a low amount of isocyanate; the water absorptivity of the polyurethane polymers is above 10%, preferably above 20%, and these polymers may range to completely gel-like, high water absorbtive polymers; these active agent polymers are useful as in medicinal, insecticidal, pesticidal, algaecidal, etc. applications; as well as zero release agents, body implants and coatings requiring hydrophilic properties; other use for the active agent systems are in sensing membranes or coatings or ion transport recognition devices such as in gaseous or liquid media; as a hydrogel providing a leachable matrix wherein the leaching agent may be body fluids, e. g., animals or human, e. g., productive livestock and domestic animals and/or pets, or animals used in medicinal or veterinary research, e. g., monkeys, mice, dogs, hamsters, rabbits, guinea pigs, cats, etc.

23 Claims, No Drawings

HYDROPHILIC OR HYDROGEL CARRIER SYSTEMS SUCH AS COATINGS, BODY IMPLANTS AND OTHER ARTICLES

This application is a continuation-in-part of application Ser. No. 277,361 filed Aug. 2, 1972, now U.S. Pat. No. 3,822,238 issued July 2, 1974.

This invention pertains to active agent carrier, release, membrane, coating and sensing systems of the active agent in combination with a polyurethane polymer; more particularly, this invention pertains to said systems wherein the combination is enhanced by polymers which absorb water; moreover, this invention pertains to articles of manufacture made therefrom and articles of manufacture from said polymers such as active agent containing systems in the form of films, sheets, sprays, shapes or forms of various configurations, coatings, granules, etc.

BRIEF DESCRIPTION OF THE INVENTION AND BACKGROUND FOR THE SAME

A. The Polymer System

Within the last few decades, the art pertaining to polyurethane chemistry has seen a tremendous growth. As a result, polyurethane polymers of various kinds and forms are fairly well known. In general terms, the polyurethanes comprise polymers formed from a resin which has an active hydrogen atom and a polyisocyanate, such as a diisocyanate. Numerous resin systems now exist which have been combined in various ratios with the polyisocyanates, and the end polymers have ranged from rigid castable shapes to soft foams. Various polymer and prepolymer reactions for preparing the above types of polyurethanes have also been developed, and these reactions are fairly well explored.

Of the many resin systems which are known and the properties of which have been described, there are continuously being added new resin systems which in combination with the polyisocyanate overcome some vexing problems encountered with other resin systems or provide better properties for a particular end use. However, many of these resin systems a priori do not predicatably function in a given polymer system; and hence, the empirical observations still are at the foundation for the development of new resin systems as well as discovery of new polymers.

In addition, the various isocyanates which have been available (or proposed to be useful without being available) give different properties in any given resin system as well as give different properties from resin system to resin system. Hence, the predictability of end polymer properties cannot be inferred from a behavior of the resin system nor the behavior of this resin system in combination of isocyanate, except in very general terms. For this reason, the proper combination of the particular resin system with the proper isocyanate and the proper interaction or intercombination with each other is still an empirical art with the unpredictable end results.

Although many carrier and transport systems are known, the present polymer system is unique because the particular water absorbtivity, i.e., hydrophilicity may be tailored to suit the particular requirements of the system. Moreover, the same family but elastic and hydrophobic polyurethane polymer systems provide ready interfacial polymer media (medium) for applications where the polymer needs to be bound lightly to tenaciously to the substrate(s) and thus the delamination separation or incompatability phenomena encountered with prior art polymers are avoided.

Thus, a polymer system capable of diversely tailored properties is presented for use in a wide variety of applications. The prior art polymer systems have offered these properties in a narrow range with often inferior results for the use recited herein.

B. The Active Agent Systems

If the above novel polymer system is now used in combination with the active agent systems, many heretofore known systems are improved or supplanted because the combination of the polymer with the active agent offers novel carrier, membrane, release, coating, sensing, ion transport, i.e., dialysis or osmosis, etc. systems.

Representative active agent systems are:
1. pharmaceuticals;
2. bacteriostats;
3. viruscides;
4. insecticides;
5. herbicides;
6. larvicides;
7. fungicides;
8. algaecides;
9. nematocides;
10. topical or dermatological agents — i.e., cosmetics, protective or screening, or moisturizing agents, etc.;
11. salts;
12. blocking agents;
13. pH regulators;
14. antifoulants for marine growth prevention;
15. screening agents, e.g., ultraviolet screening agents;
16. enzymes;
17. flavors, essences, or spices;
18. fragrances;
19. ion recognizers (reactants with);
20. humectants;
21. anti-oxidants;
22. absorbants; and
23. preservatives.

The above polymer and active agent system may be used as films or sheets in a single film or sheet combination or as multilayered film or sheet assemblage with or without a filler core and/or incorporating the above agents; as coatings either dip, tumble, or spray applied on a tablet or pill; as membranes, i.e., separating or barrier and incorporating the suitable agents from the list above; as liquid or creamy dispersions or hydrogels; as granules; as encapsulating films; as syrups; as powders, i.e., 100 mesh and smaller, i.e., to 10 micron size; as formed shapes of various configurations, e.g., rods, cubes, containing the active agent within the shape or in an interior space thereof; as inserts, i.e., body implants, pessaries, catheters; as tubes, conduits, channels, drains, screens, scrims, gauzes, etc., as conformable shapes, i.e., castable polymers with the active ingredient therein in single or multilayer.

PRIOR ART

A. The Polymer System

Numerous publications exist in the polyurethane polymer art including surveys of the prior art such as J. H. Saunders et al., *Polyurethanes, Chemistry and Technology*, Part I Chemistry, Interscience Publishers (1962). This book summarizes in part the existing prior art. A great number of publications subsequent to the date of the publication of this book including patent literature have also appeared both in this country and abroad. These publications are too numerous to mention; but in some respect or another, these have some additional illustrations of the various polyurethane precursor resins, the isocyanates, and the method of employing or making the same.

As it is well appreciated by those skilled in the art, that the issued patents in this art are too numerous to list. Inasmuch as there is disclosed in these patents in some way or another a resin system, an isocyanate, and a polymer, because of the common nature of the polyurethane polymer, these patents are all illustrative of polyurethane polymers as such. However, differences in the various polymers associated with resin systems or isocyanates, the proportions of each, linearity and branching of resin chains and funtionality dfunctionality of isocyanates, which are often thought to be obvious to the uninitiated, are far more complex and subtle and often represent painstaking investigation of critical parameters and variables. If hydrophilicity or water absorbtion has been sought for polyurethane polymers, it has more generally been sought for polymers from which foams are formed which are useful as sponges. In general, the hydrophilic polymers have been rather soft and/or non-durable.

In respect to the present invention and the polymer system aspect thereof, the prior art which pertains to the same is most closely related to producing shapes, films, sheets and coatings which are strong and desirably non-variant in properties in either dry or wet state. However, whereas the prior art as a desideratum has striven to form strongly hydrophobic systems for the reason that the strongly hydrophobic polymers display low, if any, dimensional variation in the polymer, the present polymer system is directed to a combination of properties, i.e., high hydrophilicity, excellent polymer properties in the wet state, and variations from dry to wet state which are tolerably uniform.

Of the more prevalent resin systems for producing soft hydrophilic polyurethanes, the polyethylene glycol and polyalkylene amine resin systems are known; the last two resin systems—in distinction from the polypropylene glycol resin systems which are generally hydrophobic—are used for this purpose. Further, the combination of the polyethylene glycol and polypropylene glycol resins with an appropriate, i.e., far in excess of stoichiometric requirements of isocyanate have been used to achieve sufficient softness and at the same time, sufficient hydrophobicity so that the end product would have the desirable properties. Predominantly, aromatic polyisocyanates such as toluene diisocyanate have been used as the isocyanates.

In reference to the isocyanates which have been employed in combination with the above described resins, conventional aromatic isocyanates, when reacted with the various resins, display properties which are often unacceptable for a number of reasons.

Although the unacceptable properties can be tolerated in a number of products, in other products the use of aromatic diisocyanates have been found to be acceptable as a result of price, availability, and well researched and known properties despite the instability and/or degradation of the aromatic diisocyanate in the polyurethane end polymer.

In addition to the polyurethane polymer system a now analogous polymer system used heretofore is disclosed in a series of patents directed to acrylic and methacrylic acid hydroxy lower alkyl esters or amides thereof or hydroxy lower alkoxy alkyl esters or amides thereof.

Although the acrylate hydrophilic polymer systems have been proposed for a variety of uses, the system suffers because of relative inflexibility with respect to the properties. In distinction therefrom, the polyurethane polymers allow widely diverse properties to be tailored into the polymer system suitable for the various needs and answering the requirements imposed by the various uses.

Thus, the resin part of the polyurethane molecule can be tailored either by selecting different resin components or selecting the size of the resin molecule to answer certain requirements; the isocyanate selected for its desired properties, or the two systems balanced in various proportions, by various resin mixtures and isocyanate mixtures, and these two mixtures in various proportions to each other as further outlined herein for use with the active agent.

THE INVENTION

A. The Polymer System

A number of polyurethane polymers are combined with the active agents listed above. The polymers which have the desired properties of softness and when exposed to humid atmosphere or when wet, have excellent properties in the wet state. These polymers, when in the wet state, range from gel-like polymers to polymers being compliant, soft and flexible; and in the dry state, from gel-like polymers to polymers which are machinable and polishable.

Besides numerous other beneficial properties and uses and as previously mentioned, these polymers are suitable as coatings, linings, membranes (dialysis or osmosis), absorbents, controlled release agents, swellable fabrics, gauzes, solubilizing packaging components, water transmitting coated fabrics, water swelling caulks, wet friction elastomers, artificial leather, gas filters, dentures, hair sprays, nail polishes, oil resistant shapes, etc. As coatings, the present polymers suggest themselves to the following uses: as washable surface coatings; marine paint, e.g. friction reduction coatings, antifouling agent carriers and release paints either controlled release or controlled leaching or both; antifog coatings, e.g. in diving goggles, antistatic agents; friction reducing coatings for pipes such as used for irrigation or firefighting; and shapes, either cast or machinable useful as body implants. These polyurethane polymers are derived from a unique combination of a proper resin and a proper isocyanate.

In respect to the polyurethane polymer system, it is obtained by employing a proper —OH group terminated resin derived either from ethers, esters, easters (ester-ether), or resin chains modified by various pendant, introduced, or converted groups attached to said resin chain.

For sake of easy understanding, the resin systems are based on the tabulated grouping of resins and mixtures of the same.

TABLE I

RESINS AND RESIN MIXTURES

Resin comonomer amounts tolerable in resin (low content = less than 3 moles of monomer per equivalent of —OH; high content = more than 3 moles of monomer per equivalent of —OH

| No. of —OH or amine groups contained in a compound | Monomer Unit | Ethylene oxide | Propylene oxide | Ethylene imine | Propylene imine | Dioxolane |
|---|---|---|---|---|---|---|
| —OH compounds | | | | | | |
| 2 | Ethylene glycol | any | low | any | low | any |
| 2 | Propylene glycol | high | none | high | none | high |
| 3 | Glycerol | any | low | any | low | any |
| 3 | Trimethylol propane | any | low | any | low | any |
| 4 | Erythritol | any | low | any | low | any |
| 4 | Penta erythritol | any | low | any | low | any |
| 5 | Anhydro enneaheptitol | any | low | any | low | any |
| Acids | | | | | | |
| 3 | Trimelitic acid | high | none | high | none | high |
| 3 | $H_3PO_4$ | high | none | high | none | high |
| 4 | Pyromellitic acid | high | none | high | none | high |
| 6 | Mellitic acid | any | very low | any | very low | any |
| —OH acids | | | | | | |
| 2 | Malic | any | low | any | low | any |
| 3 | Citric | any | low | any | low | any |
|  | Sugar acids | any | low | any | low | any |
| 50 units | Partially saponified polyvinyl acetate | any – high | none | any – high | none | high |
| 50 units | Polyacrylic acid | any – high | none | any – high | none | high |
| Amines | | | | | | |
| 1 | Ammonia | any | low | any | low | any |
| 2 | Ethylene diamine | any | low | any | low | any |
| 2 | Propylene diamine | high | none | high |  | any |
| 3 | Diethylene triamine | any | low | none | low | high |
| 4 | Triethylene tetramine amine | any | low | none | low | high |
| 4 | Hexamethylene diamine | high | none | high | none | high |
| 50 units | Polyethylene imine | any | low |  | low | any |

In addition to the above resins and based on the above resins, the following resins are highly water absorbtive:

a. amine and polyamine salts and quaternary compounds, wherein the salts are such as chlorides, bromides, iodides, nitrates, sulfates, oxalates, etc.; the quaternary compounds are derived from alkyl halides, benzyl halides, alkyl sulfates, alkylene oxide; and the anion may also be a chlorate, bromate, phosphate, sulfate or nitrate;

b. mixed alkoxy amines and polyamines and salts and quaternary compounds thereof of the salts and quaternary compound precursors as recited above.

In general, the lower alkyl compounds of the alkyl halides, sulfates, etc., are preferred.

Additional resins useful for the present purposes are: sulfonated maleic, itaconic, fumaric, mesoconic, citraconic esters wherein the dihydroxy precursor of said ester is preferably 2 to 4 carbon atoms, generally up to 12 carbon atoms may be in the chain of said precursor. The double bond of the unsaturated compounds after the formation of said ester is sulfonated in a manner well known to those skilled in the art. In respect to the above amine salt, quaternary ammonia salt, and sulfonate groups, the ratio of one ionic group to twenty carbon atoms furnishes sufficient water absorbtion to the polymer; lower ratios will provide increased water absorbtion to the polymer. As a convenient lower limit, one ionic group per 6 carbon atoms is illustrative.

Still other useful resins are derived from methyldiethanol amine, belonging to the group of alkyl dialkanol amines such as lower alkyl lower dialkanol amines, and a diacid. A resin falling within this group is methyl diethanol amine adipate or resins from the amine, and other diacids such as sebacic and azelaic. The amine moiety (moieties) is quaternized after the resin formation with the same precursors as listed above for quaternary ammonium compounds. Other useful acids for the above resin are maleic acid, phthalic acid, fumaric acid, itaconic acid, mesoconic acid, citroconic acid, etc.

Similarly, a resin derived from polyethylene imine such as polyethylene imine adipate may be useful as it may also be partially quaternized. Acids which may be useful for the formation of these "imine ester" resins are sebacic, azelaic, maleic, phthalic acids, itaconic, mesoconic, and citraconic acids.

In the event the polypropylene imine or polyethylene imine compounds or mixtures of the same are used, then the precursor resins may contain up to 50 imine units; these may be further modified by adducting the same with ethylene oxide, ethylene glycol, dioxolane or propylene glycol (in respect to the polyethylene imine, polypropylene glycol may be used when ionic group formation is contemplated for the polypropylene imine compounds). Thus hydrogen on the nitrogen atom in the chain may be replaced by the adducting compound. Similarly, the —OH group carrying compounds may be adducted with ethylene imine or propylene imine.

The above resins may also be admixed with polyethylene oxide adipate provided the last named resin has a molecular weight below 1000. The amount which may be incorporated should be less than 50% based on the total weight of the resin.

Still another class of resins which are useful are the sulfhydryl resins in which are introduced the sulfonium, sulfoxide or sulfone groups. Illustrative precursors of these resins are ethylene sulfide and 1,3 propylene sulfide. These resins, after formation of prepolymers with isocyanates (or the final polymers), are then converted by oxidation of the sulfhydryl group(s) to the ionic group containing resins or by alkylation to the sulfonium groups. The sulfonium group substituents are lower alkyl moieties as preferred substituents, and the electronegative element is $Cl^-$, $Br^-$ or $I^-$ or the radicle $^+OH$. In general, the sulfhydryl polymers have molecular weights from 700 to 6000 or are from 10 units to 100 units of the monomer precursor in the chain. Again, these resins should be tractable.

In respect to these resins, the equivalent weight of these is above 140, preferably above 170, i.e. up to 2000. In addition, a ratio of 2.8, preferably 2.5, carbon atoms to one oxygen atom or one amine nitrogen is still required; the lower ratio is 1.2:1 to 2.5:1 or (2.8:1). In the preferred embodiment of the range the ratio is 1.33:1 to 2.8:1, and more specifically, 1.33:1 to 2.5:1. When the above mentioned ionic groups are present, the ratios of these groups to the carbon atoms in the resin may be, in the resin portion of the final product, as stated previously. For controlling the necessary hydrophilicity, the above resins may be admixed with some more hydrophilic resins or less hydrophilic including hydrophobic resins. The less water absorbtive resins are based on comparison to the presently disclosed resins or may be hydrophobic resins which, when admixed with the water absorbtive resins, will produce the acceptable water absorbtion. Water absorbtion of the polyurethane polymer may also be controlled by the amount of isocyanate which is added to the resin. Greater amounts (compared to a base level) will increase hardness of the resin (more machinable and polishable) and also make the resin less water absorbent.

With respect to the applications such as coatings, casting films, etc., these resins may be processed in a soluble state, i.e., the isocyanate has not yet crosslinked the resin; for example, the isocyanate is incompletely reacted or is blocked (by agents such as phenols, thiourea, etc.) Thereafter, the reaction is completed and the end product becomes crosslinked in its final form. However, for purposes of this invention, the soluble intermediates, if these produce the crosslinked water absorbtive end product, are within the scope of the invention. An example of the use of noncrosslinked intermediates is in coating such as on textiles, sutures, and as a film and the reaction is completed in-situ.

Water absorption is determined by immersing the polymer in water at 20°C for 24 hours and weighing the polymer in a dry state and after removal from water and expressing the gain as % (by weight of polymer) of water absorbed.

Consequently, the disclosed excess of isocyanates, in the range set forth herein, allows the control of hardness and water pickup. In the event of low equivalent weight resins or resins having low ratio of ionic groups to carbon atoms, greater excess of isocyanates may be used as long as the desired water absorption is achieved. Also isocyanates with functionality of greater than two may be used for the above purpose and for the purpose of furnishing thermoset polymers. Difunctional isocyanates and linear difunctional resins, if used in one to one ratio, will produce thermoplastic polymers.

If a resin is used having a functionality greater than two, then the thermoset or thermoplastic nature of the polymer will be determined by the amount of isocyanate. If one isocyanate molecule is used per resin molecule, the resin will be thermoplastic; however, if in excess of one isocyanate molecule is used per resin molecule, the polymer will be thermoset. According to the present invention, in general, water soluble polymers are not desirable; water absorbtive polymers are; and the thermoset polymers are the outstanding and preferred polymers.

A listing of the above resin systems or derivatives thereof is set out below for easy visualization of the present invention.

1. An adduct of dihydroxy compounds such as ethylene glycol or propylene glycol with ethylene oxide, propylene oxide, ethylene imine, propylene imine, dioxolane or mixtures of same;

2. An adduct of trihydroxy compounds such as glycerol to trimethylol propane with ethylene oxide, propylene oxide, ethylene imine, propylene imine, dioxolane or mixtures of same;

3. An adduct of tetrahydroxy compounds such as erythritol or pentaerythritol with ethylene oxide, propylene oxide, ethylene imine, propylene imine, dioxolane or mixtures of same;

4. An adduct of polyhydroxy compounds such as anhydroenneaheptitol, sorbitol, mannitol, hydrolyzed low molecular weight polyvinyl acetate, sucrose or lactose with ethylene oxide, propylene oxide, ethylene imine, propylene imine, dioxolane or mixtures of same;

5. An adduct of polybasic acids such as trimellitic acid, pyromellitic acid, mellitic acid, pyrophosphoric acid, and low molecular weight polyacrylic and methacrylic acids with ethylene oxide, propylene oxide, ethylene imine, dioxolane or mixtures of same;

6. An adduct of hydroxy acids such as malic acid, citric acid or sugar acids with ethylene oxide, propylene oxide, ethylene imine, dioxolane or mixtures of same (sugar acids are defined in "Carbohydrate Chemistry,"Volume 5 and more specifically, Chapter 17 (a review of literature published during 1971) The Chemical Society, Burlington House, London, Great Britain (1972) and in other sources as well);

7. An adduct of amino compounds, such as ammonia, ethylene diamine, diethylene triamine, triethylene tetraamine with ethylene oxide, propylene oxide, ethylene imine, dioxolane or mixtures of same;

8. Hydrammonium or quaternary ammonium salts of 7);

9. A sulfonated polyester resin of maleic acid, itaconic acid, mesaconic acid, fumaric acid and a glycol of 2 to 6 carbon atoms;

10. A polyester of a lower alkyl dialkanolamine and a diacid wherein the diacid is adipic, sebacic, azelaic, maleic, phthalic, fumaric acid or mixtures of same, the amine group being converted to an hydrammonium or quaternary ammonium group;

11. A linear or slightly branched polyamide wherein the amine is diethylene triamine, triethylene tetramine, tetraethylene pentamine or other polyloweralkylene imines such as ethylene imine or propylene; and the diacids are maleic, adipic, azelaic, sebacic, phthalic, itaconic acid or mixtures of same (the term "slightly branched" indicates only methyl or ethyl substituents on the backbone, the ethyl substituent being less than 1%);

12. Hydrammonium or quaternary ammonium salts of 11);

13. Polysulfhydryl resin having in the backbone sulfonium, sulfoxide, or sulfone groups;

14. Hydrammonium or quaternary ammonium salts of ethylene or propylene imine adducts of polyhydroxy compounds from categories 1) to 4);

15. Polyesters of polyethylene oxides with maleic acid, adipic acid, sebacic acid, phthalic acid, azelaic acid, fumaric acid or mixtures of same.

In the event the above resin (in the polymer, when reacted with the proper amount of isocyanate) does not give the defined water absorption, then it is converted to the salt of quaternary ammonium compound if possible; if it is not possible to form a salt or quaternary ammonium compound either in the resin form or in the final polymer, then these resins are unfit as starting resins for the herein claimed polyurethane polymers. Similarly, the resins which display considerable water absorption may be reacted with greater amounts of isocyanate than the less water absorbtive resins. In combination with the functionality of the resin and isocyanate, the water absorption of resins and ability to increase or decrease the same, the proper use of the amount of isocyanate, a polyurethane polymer may be tailored to give the necessary water absorption and, in conjunction with water absorption, the properties necessary for satisfying the demands imposed by the environment in which the polyurethane polymer has to function in conjunction with the active agent.

In respect to the isocyanates, these may be represented by OCN—R'—NCO wherein R' is aliphatic including alicyclic compounds such as aliphatic, aliphatic-alicyclic, and aliphatic-aromatic hydrocarbon compounds from 4 to 26 carbon atoms, but more conventionally from 6 to 20 and generally from 6 to 13 carbon atoms. Representative examples of the above isocyanates are: tetramethylene diisocyanate; hexamethylene diisocyanate; trimethyl-hexamethylene diisocyanate; dimer acid diisocyanate; isophorone diisocyanate; hydrogenated diphenyl methane diisocyanate; methylene di(cyclohexyl isocyanate); metaxylylene diisocyanate; diethylbenzene diisocyanate; decamethylene 1,10-diisocyanate; cyclohexylene 1,2-diisocyanate and cyclohexylene 1,4-diisocyanate.

Other compounds which are useful are the isocyanate equivalents which produce the urethane linkages such as the nitrile carbonates, i.e., the adiponitrile carbonate of the formula

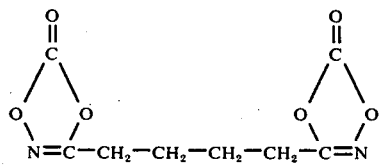

The compound is designated as ADNC and has been found as useful as the preferred isocyanates.

The preferred diisocyanate is the methylene di(cyclohexyl isocyanate) and ADNC. Other but slightly less preferred diisocyanates are trimethyl hexamethylene diisocyanate and isophorone diisocyanate.

Although the aromatic isocyanates such as 2,4 and 2,6 tolylene diisocyanate; 4,4' diphenylmethane diisocyanate; 1,5 naphthalene diisocyanate; dianisidine diisocyanate; tolidine diisocyanate; xenylene diisocyanate; tetrahydronapthalene-1,5 diisocyanate; etc. are useful for obtaining the polyurethane polymers, and these polymers have the desirable properties, the aromatic isocyanate based polymers are only useful if the degradation or if the stabilizers can be tolerated. Hence, the aromatic isocyanates are vastly less desirable.

A mole to mole ratio of resin and —NCO will produce a water soluble and fusible polymer; hence, the ratio of —NCO to resin molecules should be in about a 10%, event up to 15%, excess above the equimolar ratio, i.e., with reference to the isocyanate, from 0.02 to 0.15 in excess of the equimolar ratio in reference to the equimolar amount of said isocyanate. Or expressed on another basis and providing another range in an amount from 0.02 in excess of one equivalent weight of isocyanate times its functionality per equivalent weight of resin times its functionality up to equi-equivalent weight of said isocyanate to said resin. Still another way for expressing the last range is: wherein the isocyanate is in an amount from 0.02 to 0.15 in excess of the equimolar amount of isocyanate divided by its functionality per 1 mol of resin divided by its functionality. If the isocyanate is used in greater excess for the same resin, water pickup of the polymer will decrease. However, some resins (high equivalent weight) will tolerate considerable increase of the isocyanate above the equimolar ratio, even as high as equal equivalents. Additionally, a prepolymer may be reacted with the resin in addition to the isocyanate such as a polyethylene oxide and isocyanate prepolymer. However, the minimum water absorption of the end polymer should be at least 10%. The ethylene oxide may be up to 100 units in the prepolymer; a prepolymer of 4 ethylene oxide units is a convenient lower range for the prepolymer, although the lowest unit may be ethylene glycol as a derivative of ethylene oxide. The polyol may be as low as 10% by weight when a prepolymer is used and as high as 40% by weight based on the total weight of polyol and prepolymer.

When reacting the resin with the isocyanate, either a one-shot or a prepolymer reaction procedure may be followed. The reaction is carried out by heating the reactants for the appropriate length of time; the reaction may also be accelerated or controlled by appropriate catalysts such as stannous octoate, dibutyl tin salts, DABCO, or other tertiary amines or compounds recognized as catalysts for urethane reactions and well known in the art. The polymer may be prepared in bulk, in solution or in suspension.

For purposes of the present invention, in the polymer system the resin system is a tractable, i.e. a workable, resin system for a reaction with the isocyanates. A workable resin system is one which is formed of the resin and a solvent or a resin which is a liquid or can be liquified at a reasonable working temperature, e.g. up to 100°C. A preferred solvent is dimethylformamide, dioxane or butyrolactone.

In placing the present polymer system in its proper context, while it is known that the prior art polyurethanes which are derived from a so-called "soft" resin can be hardened by using increased amounts of isocyanate, with the concomitant decrease in hydrophilicity, the present invention has been achieved by using a proper and low ratio of isocyanate to resin ratio. The observed phenomenon of the increase in hardness and concomitant hydrophobicity of the polymer by increase of isocyanate to resin ratio has been counteracted in the present invention, in distinction from the prior art, by the proper incorporation of the water absorbtive moieties in the resin, proper selection of molecular weights, equivalent weights, and the discovery of the proper chemical structure of the polymer with the end result being a polymer system having great increase in water pickup and at the same time the desired physical properties.

As a consequence, the polyurethanes have answered the desired need for a polymer which has the parameters acceptable for manufacturing articles of commerce such as listed above under the conditions of the present day technology and eminently suitable for the recited uses in combination with the acitve ingredients or other uses.

In illustrating the above polymers which are useful for the enumerated application, the so-called Hydron (trademark of National Patent Development Corporation, New York, New York), a hydrophilic acrylic resin base polymer is a convenient benchmark. The properties of the present polymers compare very favorably and most advantageously with the Hydron polymers. These properties will now be further amplified. In general, the polymer may have a water pickup in excess of 10%, preferably in excess of 20%. A polymer having a 20% water pickup is preferred because at or above this degree of water absorption, the polymer may be usefully employed to simulate the many natural polymers or membranes existing in plants or living beings. Generally a water absorption of 37% or more by weight is rather easily achieved. The polymer may be cast or shaped by techniques well known in the art such as used for films, sheets, deposits, extrusions, pressure casting, etc. For appropriate marine coatings which may have a base polymer such as in Example 19 and which may be active agent leaching coatings, the disclosure in U.S. Pat. No. 3,575,123 is explanatory of the uses for which the present polymers are suitable. However, the present polymers are far more durable and versatile and can be tailored to meet specific design goals.

In furnishing an illustrative embodiment of the polymer system, the following examples not only illustrate but also amplify the above described polymer system; however, the examples herein are for the purpose of illustrating the invention which invention is to be viewed from all the present disclosure and not merely from the examples describing the polymer.

EXAMPLE 1

Resin 1. 134 grams (1 mole of dipropylene glycol were placed in a flask with a gas inlet and a stirrer. The ethylene glycol was heated at 110°C and a vacuum of about 10 mm Hg was applied to it to dry it thoroughly. 0.5 gram solid NaOH was added and the mixture was stirred until the NaOH dissolved. 560 grams (12.7 moles) of ethylene oxide were distilled into the reactor through the gas inlet at such a rate that the pressure in the reactor remained constant at 1 atmosphere. When all of the propylene oxide had been added, $CO_2$ gas from dry ice was added to neutralize the NaOH. The resulting resin has a molecular weight of 694 and a C:O ratio of 2.03:1.

Polymer 1. 69.4 grams (0.1 mole) of Resin 1 were reacted with 28.8 grams (0.11 mole) of Hylene W (a light stable diisocyanate having an equivalent weight of 131, produced by DuPont) by heating the two together for 48 hours at 100°C. The product was a soft resin which swelled slightly in water.

EXAMPLE 2

Resin 2. 124 grams (2 moles) of ethylene glycol were dried by storing over 4A molecular sieve. 0.01 gram boron trifluoride etherate was added and the temperature was raised to 55°C. 592 grams (8 moles) of dioxolane were added dropwise at a rate such that the temperature did not exceed 60°C. The reaction mixture was maintained at 55°C overnight, yielding an oily liquid having a molecular weight of 310 and a C:O ratio of 1.4:1.

Polymer 2. 31 grams (0.1 mole) of Resin 2 were reacted with 23.1 grams (0.11 mole) trimethyl hexamethylene diisocyanate by heating for 8 hours in the presence of 0.01 gram stannous octoate, yielding a rubbery polymer which swelled greatly when immersed in water.

EXAMPLE 3

Resin 3. The procedure for Resin 1 was repeated with 62 grams (0.67 mole) glycerol and 632 grams (9 moles) of propylene oxide, yielding an oily resin with a molecular weight of 1035 and a C:O ratio of 2.62:1.

Polymer 3. 103 grams (0.1 mole) of Resin 3 were reacted with 28.8 grams (0.11 mole) of Hylene W by the procedure disclosed for making Polymer 1 (above), yielding a rubbery polymer which absorbs more water than Polymer 1.

EXAMPLE 4

Resin 4. The procedure for making Resin 2 was repeated with 92 grams (1 mole) of glycerol and 222 grams (3 moles) of dioxolane, yielding a resin with a molecular weight of 314 and a C:O ratio of 1.33.1.

Polymer 4. 31.4 grams (0.1 mole) of Resin 4 were reacted with 282 grams (0.11 mole) of Hylene W according to the procedure for preparing Polymer 1. This polymer is hard and resinous and absorbs water and softens to a rubbery state in water.

EXAMPLE 5

Resin 5. 45 grams (0.33 mole) of trimethylol propane were reacted with 955 grams (13 moles) of dioxolane according to the procedure for preparing Resin 2, yielding a waxy resin having a molecular weight of 3000 and a C:O ratio of 1.52:1.

Polymer 5. 100 grams (0.1 equivalent, 0.033 mole) of Resin 5 were reacted with 10.5 grams (0.1 equivalent, 0.05 mole) of trimethyl hexamethylene diisocyanate by dissolving the resin and isocyanate in 250 grams dry dimethyl formamide and heating at 110°C for 48 hours. The product was an elastic gel. The dimethyl formamide was leached out of the polymer with water, leaving a soft, rubbery gel containing about 70% water. On drying, a strong, soft rubbery polymer remained.

EXAMPLE 6

Resin 6. 122 grams (1 mole) of erythritol were reacted with 464 grams (8 moles) of propylene oxide according to the procedure for making Resin 1, giving a product with a molecular weight of 686 and a C:O ratio of 2.33:1.

Polymer 6. 58.6 grams (0.1 mole) of Resin 6 were reacted with 28.8 grams (0.11 mole) Hylene W according to the precedure for making Polymer 1. The product was a hard resinous solid which softened in water and swelled.

EXAMPLE 7

Resin 7. 250 grams (1 mole) of pyromellitic acid were dispersed in 222 grams of dry dimethyl formamide. 0.25 grams of NaOH was added and the temperature was raised to 110°C. 528 grams (12 moles) of ethylene oxide were distilled into the reactor, yielding a resin having a molecular weight of 778 and a C:O ratio of 1.4:1. This resin is stored as a 77.8% (1 molar) solution in DMF.

Polymer 7. 100 grams of Resin 7 solution, containing 77.8 grams (0.1 mole) of Resin 7, were reacted with 23.1 grams (0.11 mole) of trimethyl hexamethylene diisocyanate by the method disclosed for preparing Polymer 5. After leaching the DMF out and drying, the polymer was strong and hard, but softened and swelled in water.

EXAMPLE 8

Resin 8. 192 grams (1 mole) of citric acid were reacted with 155°C with 3080 grams (86 moles) of ethylene oxide according to the procedure for making Resin 1. The resin formed was a waxy solid having a molecular weight of 4000 and a C:O ratio slightly below 2:1.

Polymer 8. 100 grams (0.025 mole, 0.1 equivalent) of Resin 8 were reacted with 13.1 grams (0.05 mole, 0.1 equivalent) of Hylene W according to the procedure for preparing Polymer 5. The properties of the polymer were similar to Polymer 5.

EXAMPLE 9

Resin 9. 360 grams (0.1 mole, 5 equivalents) of a polyacrylic acid with a 50 degree of polymerization were dissolved in 420 grams of dimethyl formamide. 220 grams (5.0 moles) of ethylene oxide were added according to the method for preparing Resin 7, yielding a resin with a molecular weight of 5800 and a C:O ratio of 1.67:1, as a 0.1 molar solution in DMF.

Polymer 9. 100 grams (containing 58 grams, 0.01 mole) of Resin 9 solution were reacted with 2.88 grams (0.11 mole) of Hylene W according to the procedure disclosed for preparing Polymer 5. The polymer thus formed was hard and resinous, but swelled and absorbed several times its weight in water after being worked up the same as Polymer 5.

EXAMPLE 10

Polymer 10. Polymer 9 synthesis was repeated using 21.0 grams (0.10 mole) of trimethyl hexamethylene diisocyanate in place of the Hylene W. The polymer was harder and absorbed less water than Polymer 9.

EXAMPLE 11

Resin 10. 136 grams (1 mole) of triethylene tetramine were reacted with 264 grams (6 moles) of ethylene oxide by distilling the ethylene oxide into the triethylene tetramine at 80°C. The resulting product was a viscous liquid resin having a molecular weight of 300 and a C:(O+N) ratio of 1.8:1.

Polymer 11. 30 grams (0.1 mole) of Resin 10 were reacted with 28.8 grams (0.11 mole) of Hylene W according to the method disclosed for preparing Polymer 1. The polymer was hard and resinous, but softened in water.

EXAMPLE 12

Resin 11. 30 grams (0.1 mole, 0.6 equivalents) of Resin 10 were reacted with 570 grams (13 moles) of ethylene oxide according to the method for preparing Resin 1, yielding a waxy resin with a molecular weight of 6000 and a C:(O+N) ratio of slightly less than 2:1.

Polymer 12. 100 grams (0.017 mole, 0.1 equivalent) of Resin 11 were dissolved in 100 grams of dimethyl foramide and was reacted with 8.7 grams (0.1 equivalent) of toluene diisocyanate, forming a polymer which was soft and rubbery after removal of the dimethyl formamide. The polymer swelled to several times its starting volume when immersed in water.

EXAMPLE 13

Polymer 13. 58.8 grams (0.1 mole) of Polymer 11 (containing 0.4 moles amine nitrogen) were heated for 24 hours at 100°C with 24.6 grams (0.2 mole) of benzyl chloride. The product thus obtained swelled more in water than did Polymer 11.

EXAMPLE 14

Polymer 14. 30 grams (0.1 mole) of Resin 10 were dissolved in 50 grams dimethyl formamide. 20.5 grams (0.09 mole) adiponitrile dicarbonate was added and the solution was heated at 110°C until the evolution of carbon dioxide stopped. The resulting viscous solution, containing a polymer with a calculated molecular weight of about 5000 was reacted with 4.2 grams (0.02 mole) of trimethyl hexamethylene diisocyanate. The polymer, after removal of the dimethyl formamide and drying, was hard and resinous, but swelled in water.

EXAMPLE 15

Resin 12. A polyester resin was prepared by reacting 588 grams (6 moles) of maleic anhydride, 875 grams (6 moles) of adipic acid, and 807 grams (13 moles) of ethylene gylcol at 200°C with a nitrogen purge to remove water. The resulting polyester had a molecular weight of 2162 and a hydroxyl equivalent weight of 1081. It has a double bond equivalent weight of 360.

Polymer 15. 21.6 grams (0.01 mole) of Resin 12 were reacted with 5.0 grams (0.020 mole) methylene diphenyl isocyanate by heating the two together at 30°C for 8 hours, forming an isocyanate terminated prepolymer. The prepolymer was cast in a thin film and allowed to cure by reaction with atmospheric moisture. the polymer film was a firm elastomer. The cured film was boiled with a 10% aqueous solution of sodium bisulfite for 45 minutes, during which time the film expanded in area. The film shrank and became hard and brittle when dried, but softened and swelled in water.

EXAMPLE 16

Resin 13. 1260 grams (8.6 moles) of adipic acid and 1140 grams (9.6 moles) of methyl diethanolamine were reacted at 200°C to form a tertiary amine containing polyester resin with a molecular weight of 2090, a hydroxyl equivalent weight of 1045, and an amine equivalent weight of 243.

Polymer 16. 104.5 grams (0.1 equivalent, 0.05 mole) of Resin 13 was reacted with 9.6 grams (0.11 equivalent, 0.0505 mole) toluene diisocyanate and 54 grams benzyl chloride by heating the mixture at 110°C for 8 hours. The polymer thus obtained was hard and brittle, but swelled to form a soft gel in water.

EXAMPLE 17

Resin 14. 136 grams (1 mole of triethylene tetramine were reacted with 146 grams (1 mole) of adipic acid by heating at 200°C until the reaction mixture reached a viscosity of about 200 cps at the reaction temperature. On cooling, the resin solidified to a glassy mass. The molecular weight was not measured, but is estimated to be 10,000. The C:(N+O) ratio is 2:1 and the amine equivalent weight is 128.

Polymer 17. 100 grams (about 0.01 mole, 0.77 equivalents NH) of Resin 14 were reacted with 15.1 grams (0.06 moles) of Hylene W by heating the mixture for 8 hours at 110°C. The polymer, which is rubbery, swells slightly in water. When acid is added to the water, the polymer forms an amine salt which swells much more and absorbs more water. On drying, the same salt of the polymer is hard and brittle.

EXAMPLE 18

Resin 15. 182 grams (1 mole) of sorbitol were reacted with 696 grams (12 moles) of propylene oxide according to the procedure for preparing Resin 1, forming a viscous liquid resin with a molecular weight of 878 and a C:O ratio of 2.3:1.

Polymer 18. 87.8 grams (0.1 mole) of Resin 15 were reacted with 23.1 grams (0.11 mole) of trimethyl hexamethylene diisocyanate according to the procedure disclosed for preparing Polymer 1. The polymer is hard and resinous and swells in water.

EXAMPLE 19

Resin 16. 18.2 grams (0.1 mole) of sorbitol were reacted with 572 grams (13 moles) of ethylene oxide according to the method disclosed for preparing Resin 1, yielding a resin with a molecular weight of 6000 and a C:O ratio slightly less than 2:1. The resin is waxy and melts to a moderately viscous liquid at about 45°C.

Polymer 19. 60 grams (0.01 mole, 0.06 equivalent) of Resin 16 and 10.5 grams (0.06 mole, 0.12 equivalent) toluene diisocyanate were reacted by heating at 80°C for 4 hours, forming an isocyanate terminated prepolymer. The prepolymer was dissolved in sufficient dry methyl ethyl ketone to obtain a viscosity of 2000 cps. This solution was painted onto a wood surface and allowed to cure by atmospheric moisture. The coating was strong and resilient, and water spread on it.

EXAMPLE 20

Resin 17. 158 grams (1.4 moles) of 1,3 dichloro propane were dissolved in 158 grams of dioxane. A saturated solution of 117 grams (1.5 moles) of $Na_2S$ in water was mixed with the dioxane and the liquids were boiled together for 4 hours. The polymeric product, after washing with HCl, had a molecular weight of 1030 and a C:S ratio of 3:1. It is a SH terminated polythioether.

Polymer 20. 10.3 grams (0.01 mole) of Resin 17 was mixed with 1.94 grams (0.01 mole) of toluene diisocyanate and the mixture was cast into a thin film and allowed to cure at 100°C for 8 hours. The cured film, which was rubbery, was immersed for one half hour in 3% hydrogen peroxide solution. The polymer film swelled. The oxidized film, which contains sulfone groups, shrinks and becomes hard on drying, but swells and softens in water.

EXAMPLE 21

Resin 18. 122 grams (1 mole) of erythritol were reacted with 516 grams (12 moles) of ethylene imine according to the method disclosed for preparation of Resin 2, forming a resin having a molecular weight of 638 and a C:(O+N) ratio of 1.75:1.

Polymer 21. 63.8 grams (0.1 mole) of Resin 18 were reacted with 28.8 grams (0.11 mole) of Hylene W by mixing the two at room temperature and gently warming until the mixture became clear. The polymer is hard and resinous in the dry state and swells and softens in water. When the water is acidified, the polymer swells further.

EXAMPLE 22

Resin 19. 182 grams (1.0 mole) of sorbitol was reacted with 342 grams (6 moles) propylene imine according to the method disclosed for preparation of Resin 2. The product was a viscous liquid with a molecular weight of 542 and a C:(O+N) ratio of 2:1.

Polymer 22. 54.2 grams (0.1 mole) of Resin 19 were reacted with 28.8 grams (0.11 mole) of Hylene W by the method of Polymer 21. The properties of the polymer are similar to those of Polymer 22 except that it swells in water to a smaller extent.

EXAMPLE 23

Resin 20. 960 grams (6.6 moles) of adipic acid were reacted with 1475 grams (7.6 moles) or tetraethylene glycol to form a polyester with a molecular weight of 2217 and a C:O ratio of 2:1.

Polymer 23. 222 grams (0.1 mole) of Resin 20 were reacted with 27.5 grams (0.11 mole) of methylene di-(phenylisocyanate) by heating at 110°C for 24 hours. The polymer, which is elastomeric, swells in water and becomes softer.

B. The Active Agent System

With reference to the polymers described and exemplified above and the combination of same with the active agents, the support for the various active agents will now be illustrated.

With respect to the pharmaceuticals, bacteriostats, viruscides, fungicides, insecticides, nematocides, and herbicides, the active agents suitable for incorporation with the polymers disclosed herein are disclosed in U.S. Pat. 3,576,760; the disclosure of this patent is incorporated by reference herein and made part of the disclosure herein for the necessary support. Further therapeutically active material useful in the dossage units further mentioned herein are disclosed in U.S. Pat. Nos. 3,577,512; 3,641,237; and 3,641,237, the disclosure of which is incorporated by reference herein; the algaecides are disclosed in U.S. Pat. No. 3,633,546, the disclosure of which is incorporated by reference herein.

Still further as a further embodiment, the disclosures in U.S. Pat. Nos. 3,576,760; 3,567,118; and 3,400,890, as these pertain to fragrances, food flavors, enzymes, and vitamins are incorporated by reference herein. With respect to vitamins, U.S. Pat. No. 3,574,826 further discloses the available vitamins, again this patent is incorporated by reference herein.

With respect to marine coatings and antifoulants, these are disclosed in U.S. Pat. No. 3,575,123 previously mentioned above, the disclosure of which is incorporated by reference herein.

With respect to cosmetic agents including protective screening (e.g., ultraviolet and sunburn preventors), these are disclosed in U.S. Pat. Nos. 3,697,643, 3,574,822, and 3,577,518, the disclosures of which are incorporated by reference herein.

Salts which may be incorporated in the polymer to provide a leachable matrix include many of the common acid and base salts, e.g., alkali chlorides, bromides, etc., e.g., lithium chloride, salts of weak acids and strong bases and salts of strong acids and weak bases useful as pH control agents, e.g., the sodium salts of the various acids of phosphorus.

Of the anti-oxidants and preservatives, these are the commonly employed and used food preservatives on the approved list of additives for food kept by Food and Drug Administration and incorporation by reference herein.

Industrial antioxidants such as thiourea and dithioerythritol are within the scope of the present invention.

As ion recognizers, the commonly used titrating dyes for the specified ranges and conditions are suggested. These dyes generally change the appearance within a particular pH range and upon encountering either specific ion species or merely show the appropriate pH level.

As absorbants, commonly used absorbants such as charcoal, alumina, zirconia and molecular sieve material may be incorporated within the present polymer system.

As humectants, the polymer may be admixed with a polyhydric alcohol, e.g., propylene glycol, glycerine, etc.

Other applications in which the polymer-active agent combination may be used are such as nutrient media, catalysts, e.g., water soluble catalysts, coloring agents, and thickening agents.

C. General Method for Preparation of the Polymer-Active Agent Combination

With respect to the polymers recited above, these are first selected according to the criteria established above for the water absorbtivity, and secondly selected according to the desired physical properties, the desired ratio of cross-linking, i.e., use of the thermoset properties (hardness) imparted by the isocyanate to the polymer. The water permeability, absorbtivity, hardness of polymer, etc., are determined and appropriate work-up procedure is established.

Thus, the polymer may be prepared and dissolved in a suitable solvent mentioned above and then the active agent incorporated in the polymer. Thereafter, the polymer may be cast as a syrup and the solvent removed.

Similarly, the polymer may be prepared by first incorporating an inert (inert with respect to the polymer precursors) active ingredient in the resin and then the mixture reacted with isocyanate and then casting, shaping, extruding, etc. of the admixture carried out in the conventional manner.

Still further, the active ingredient may be dissolved in a solvent suitable for the polymer, the polymer then dissolved and the admixture cast and formed as desired in sheets, shapes, configurations, films, foils, and the like. If the active agent possesses a moiety capable of reacting within isocyanate, the same is incorporated in the polymer after formation of the polymer. The active moieties are those defined as active hydrogen moieties. These moieties are ascertained by methods well known in the art.

As another embodiment, the polymer system may be dissolved and then used as a coating for granulated material by dispersing or by spraying the mixture in a vacuum or spray drying tower.

Repeated coating operations with the above polymers of different properties provides a granule with a coating having a designed or tailored release rate.

Alternatively, the polymer with the active material within it as cast may be ground such as in a solid state (low temperature grinding) and the pulverized material then coated, suspended, or incorporated with a diluent if necessary in a suitable tablet form.

In a similar manner, the active ingredient may be incorporated in the liquid polymer or prepolymer and the polymer further reacted and then extruded or blow molded to form a desired shape as it is well known in the art.

With respect to the active ingredient release activity, it is designed by establishing an appropriate time versus amount of agent released curve for each of applications in the medium employed. Similarly, release activity under controlled conditions may be measured such as in a standard culture dish for pharmaceutical applications. In addition, the residual amount may be established for the various active agents under dynamic conditions, e.g., in a conduit having a certain flow rate of fresh fluid.

In any of the applications, the release rate may be tailored according to the water absorbtion rate of the polymer, diffusion path or wall thickness of the polymer surrounding the active constituent, and the amount of the active ingredient in the polymer on a weight percent basis.

With respect to body implants, a suitable active agent may be incorporated in the polymer then shaped to the desired form and then placed in the body cavity, or in tissue, muscle, etc. Inasmuch as these polymers retain a large percentage of water relative to the weight of dry substance, these polymers are elastically deformable under relatively small pressure but virtually immune to plastic deformation. These polymers as semipermeable membranes permit passage of water and certain dissolved materials. Thus, these polymers may be used in the form of pessaries, tubes, rods, films, etc. or can be shaped with a hollow part(s) and the hollow part(s) filled with the desired active agent. Reinforcing components may be incorporated in the structure.

As part of the general method, blocking layers may be employed in conjunction with the polymers. These blocking layers may be of ingestible materials conventionally employed, e.g., waxes such as beeswax, carnauba wax, bayberry wax, Japan wax; higher fatty alcohols such as cetyl alcohol, stearyl alcohol; higher fatty acids such as oleic acid, palmitic acid, and stearic acid; higher fatty acid esters such as glyceryltristearate, cetyl palmitate, diglycol stearate, glycerol myristate, triethylene glycol monostearate; Carbowaxes; polyethylene glycol esters of the above fatty acids or mixtures of these. Generally, the blocking agents are 0.1 to 5 mils thick.

With respect to zero order release forms of the polymer and active agent, the polymer in these is from 0.2 to 10 mils thick, usually at least 0.5 mils thick.

Usually 0.1 to 35% by weight based on the polymer of the entrapped active agent is employed. Higher amounts are used where high concentrations are desired such as for antifoulant uses. However, it may be necessary to dilute the admixture with a solvent, e.g., acrylic lacquer thinner, to make the same suitable for application; because above 30 % by weight of solids in the polymer, the viscosity of the polymer is high, that is, the polymers and active agent admixture become less tractable.

With reference to the following Examples, these are to illustrate the invention and various facets of the above described embodiments.

EXAMPLE A

The resin of Example 1 was used to prepare the following antibiotic combination. 69.4 grams of resin and 1.28.8 grams of Hylene W (a light stable diisocyanate having an equivalent weight of 131, produced by DuPont) is mixed together with phenoxyethyl penicillin in an amount to provide for gradual release of 1,200,000 units per gram of casting syrup. The cast product is formed in either shape, e.g., a film form, or powdered form, and is employed as a pharmaceutical carrier for the antibiotic, thus forming a layer. The use of a casting syrup for a shaped or powdered preparation has the advantage that it prevents deterioration and loss of potency to which the antibitotic is subject in conventional pharmaceutical carriers, thereby extending the shelf life or expiration date of the antibiotic preparation.

The polymerization of the casting syrup to a solid can be completed by heating to 70° to 80°C. The product can omit the antibiotic and serve merely as an outer coating for penicillin.

EXAMPLE B 5 grams of the polymer mix used in A above is mixed with 500 miligrams of ascorbic acid. This mixture is cast in the form of a cylinder 1 cm by 7 cm. After removing from the mold, a cylinder suitable for use in the invention to provide prolonged release of the ascorbic acid is obtained.

EXAMPLE C 69.4 grams of resin 1 from Example 1 above is mixed with 28.8 grams of Hylene W and heated for 10 hours at 100°C. The resulting polymer is then diluted in methanol and is then added to four times its volume of water with vigorous agitation, the white precipitate so obtained was isolated by filtration and dried to yield 11 grams of polymer. This polymer is soluble in methanol, ethanol, glycols, tetrahydrofurane, dimethylsulfoxide, etc.

EXAMPLE D

Example B is repeated using the same quantities of resins and reactants but adding to the mix 0.5 parts of aspirin and then is cast into a mold and is polymerized to form a film.

EXAMPLE E

Resin of Example 1 above is mixed with 28.8 grams of Hylene W, is cast into a mold, and polymerized at 70° to 80°C to form a film, this film may be dissolved in DMF and used as a coating for herbicide granules, or the materials recited under the heading "The Active Agent System" at the beginning of the specification, i.e., items 1 to 23.

EXAMPLE F

The polymer of Example C is dissolved in ethanol to provide a solution containing 15 % solids. In 100 grams of the solution were dissolved 3 grams of pencillin and the solution dried as a thin film on a rotating evaporator.

EXAMPLE G

A 2 liter reaction vessel equipped with an electric mantle, an electric stirrer, and a $CO_2$ inlet tube and a condensor was charged with 69.8 grams of Carbowax 1540, 7.64 grams of diethylene glycol, 31.6 grams of Hylene W and 1200 grams of toluene. The solution was heated and stirred under carbon dioxide at reflux for 18 hours. The reaction was then cooled to room temperature and the toluene decanted off from the solid layer. The solid product was dissolved in methanol, filtered, and precipitated by addition to 4 liters of rapidly stirred water. This product was further washed in additional distilled water and finally allowed to dry at reduced pressure. the polymer was then further purified by redissolving in methanol at 20 to 30 % concentration and reprecipitating in four volumes of rapidly stirring water, washing in distilled water and drying at reduced pressure. The yield of dry polymers was 95%.

EXAMPLE H

Solutions of the different polymers obtained in Examples A to G are prepared by mixing 56 grams of the dry polymers with 130 grams ethyl alcohol (95%) and 24 grams distilled water in a blender. Trapped air bubbles were freed by letting the solution stand.

Multilayer films of each polymer were coated on a horizontal casting table lined with polyethylene film which had been washed with benzene and ethanol.

A 12 mil thick layer of polymer is spread on the casting table with an applicator. the wet film is immediately covered to insure a slow rate of evaporation of the solvent at room temperature.

The films are allowed to dry during 5 hours before these are top coated with a 5 mil thick layer of high release rate polymer as prepared in Example G, and allowed to dry during one hour. The resulting films are then removed from the casting tables and stored at room temperature for further use (20°C, 60% relative humidity). The resulting bilayer films are homogeneous and 3 to 4 mils thick. The mechanical properties are dependent upon the composition of the various layers as previously set forth while a drug is preferably incorporated entrapped in a hydrophilic polymer as a layer, the drug can be used alone. Thus, procaine pencillin G in the form of a powder can be covered by a multifilm layer of the type shown in Example H using the polymer of Example 1. The film was wrapped around the drug in the form of a pouch and sealed to enclose the drug.

EXAMPLE I 300 mg. Pilocarpine base is added to a solution of 800 mg. of polymers as prepared in Example G in 4000 mg. of ethyl alcohol (95%). The mixture is stirred with a magnetic stirrer during one hour and a layer of the homogeneous alcoholic solution was spread with an applicator having a 10 mil clearance, as described above. The film is allowed to dry at room temperature during 1 hour, then under reduced pressure for 2 additional hours. The resulting dry film is 2 mils thick and could be cut to any desirable shape. This film, when it is placed in water, displays fast release of Pilocarpine base. 1 $cm^2$ of the core film prepared above releases 1.5 mg. Pilocarpine base within 2 hours when placed in water at 37°C.

EXAMPLE J

A square piece of core film containing pilocarpine base as prepared in Example I is laminated between 2 square pieces of the barrier film (1.5 cm × 1.5 cm) as prepared in Example 8, the highly permeable coating forming the external layer. The resulting laminate structure is slightly pressed to expel trapped air bubbles and edges are sealed. The resulting insert has a total thickness of 8 to 10 mils. Four such laminates are made using the different polymers of Examples 1, 4, 5, and 6.

For certain uses, the maximum thickness of the 2 or 3 layer laminate is 20 mils. For other uses, however, there is no critical limit in the thickness, e.g., thicknesses of 100 mils, 250 mils, or even more can be used for the laminate.

EXAMPLE K

Determination of the Elution Rate of Philocarpine Base

Inserts are prepared as described above in Example J and are introduced into vials each containing 6 ml of a solution of sodium chloride (0.9%) in distilled water, and the vials are kept at a constant temperature of 37°C. in a thermostated water bath. The concentration of eluted Philocarpine base in water is determined with a Beckman DB-A spectrophotometer using the maximum absorption of Pilocarpine at 215 Mu. Elution rates are checked over periods of 24 hours and are found to be dependant on the composition of the polymer forming the barrier film. Moreover, for the same polymer used, the solution rate is dependant on the thickness of the barrier film.

For typical barrier films made of polymers prepared in Examples 1, 4, 5, and 6, the rate of release of Pilocarpine base is found constant over more than 24 hours, ranging from 5 to 50 micrograms of Pilocarpine base per hour according to the composition and the thickness of the barrier film used in the preparation of the insert.

The elution rate is capable of being kept constant for periods as short as an hour, or as long as a week or longer so long as sufficient drug is provided.

Prior to use, the laminate or film-coated drug of the present invention has a greater stability and longer shelf life than similar drugs devoid of the barrier film. As a result, deterioration and loss of potency are reduced.

The products of the present invention are useful not only for body cavity inserts or topical application, but can be used as implants, e.g., in humans, cattle, sheep, guinea pigs, pigs, dogs, cats, etc. to provide sustained zero order release of appropriate drugs such as those set forth above, e.g., cortisone phosphate disodium, phenobarbital sodium, nicotinamide, etc.

Hydrogels having a broad range of unusual physical and chemical properties may be obtained by suitable selection of reactants. The mechanical properties and the ability of retaining water as a homogenous constituents are outstanding.

Hydrogels obtained from the reactants of this invention are distinguished by excellent resistance to chemical attack. Their polymer constituent is not hydrolyzed by the water which becomes an integral part of the hydrogel. Those cross-linked polymers with acid of base groups are not readily attacked by inorganic acids or bases, but rather alter their degree of water up take. Solution grade material of the invention without acid or base modification are also not degraded by acids or bases.

This chemical inertness together with colloidal properties and physical properties can be very closely assimilated to those of living tissue which make the hydrogels of the invention and objects made therefrom eminently suitable for the purposes of surgery.

Further, the hydrogels of this invention may be cured to form solid or shaped bodies such as rod sheets, tubes, and other articles and will be hereinafter further described.

Additionally, the process has resulted in polymers with up to 98% conversion of active agents and polymers and has resulted in materials capable of absorbing excessive amounts of water (more than 20% and up to 90% and even higher than 150% when fully equilibrated in aqueous solution).

Additionally, the hydrophilic polymer provides an excellent industrial filter medium in that it has the ability to retain and release other components, such as thiourea or dithioerythritol, which are stable against oxidation and are therefore available for reaction with the toxic, irritant, or odorous combustion products of exhaust smoke to eliminate it or modify it to a nonobjectionable form. Such components need only be soluble in the polyhydric alcohol, alcohol, or water which is carried by the hydrophilic filtering medium. Thus, absorption of a reaction with nitrous oxide or other nitrogen oxides, hydrocarbons, and other combustion products in the base can be obtained.

The hydrophilic polymers can also be readily employed as a filter medium for use as a chromatographic filter by means of its ability to absorb water soluble pigmented stain or color components. Further, the hydrophilic polymers of this invention may be made with inorganic groups and as such, in small particle size would act as an absorbant media as well as an ion exchange resin.

The hydrophilic polymers may also be employed in the form of a covering, bandage, or dressing with or without having entrapped therein a medicinally active substance, which if incorporated, would be slowly released. Such film, whether laid down as a free film, or from a solution, would have very high moisture vapor transmitting properties. The dressings prepared as film may be backed with an adhesive and used as a surgical drape, bandage, etc. Such films are preferably not reinforced, however, if so desired, such films could have a flexible reinforcing member embedded therein.

In still another form of the invention, the hydrophilic polymer is adapted to carry water soluble nutrients which can be released under controlled conditions. Thus, agar plates can be formed to carry the water soluble elements necessary. The plates are dried. The nutrient is then available for substantially instant use upon wetting the plates in water. Such plates may be used for culturing organisms, tissue, etc.

Further examples are illustrated herein.

EXAMPLE AA 2.08 grams resin 1, plus 0.86 grams Hylene W is added to 100 milligrams of norethandrolone (Nilevar). This syrup is cast in the form of a cylinder 1.3 cm by 2.5 cm. and is polymerized at 70°–80°C for 30 hours. After removing from the mold, a cylinder suitable for in vivo implantation to provide prolonged release of the norethandrolone (Nilevar) is obtained for use in animal husbandry.

EXAMPLE BB 69.4 grams of resin 1 from Example 1 is mixed with 28.8 grams of Hylene W and heated for 10 hours at 100°C. The resulting syrup is added to four times its volume of water with vigorous agitation and the white precipitate so obtained is isolated by filtration and dried to yield 11 grams of polymer. This polymer is soluble in methyl alcohol.

Discs of hydrophilic polymer prepared as shaped articles from this solution measuring ¼ inch in diameter and 0.05 mm. in thickness, are saturated with an antibiotic solution of Bacitracin and tested against strains on agar plates. It is observed that inhibition of the standard strains occured as predicted and that multiple transfers still showed inhibition of strains. From the results, it becomes apparent that the elution of the agent from the hydrophilic polymer discs is a gradual process and extends over a significant period of time.

EXAMPLE CC 69.4 grams of resin 1 from Example 1 are mixed with 29.8 grams of Hylene W, the mixture is cast and cured to form a hollow cylinder 60 mm long, with an outside diameter of 5 mm and walls 0.5 mm thick. The hollow interior of the cylinder is filled with 1160 mg of norethandrolone (nilevar), and hole is sealed with an additional casting polymer, cured, and the cylinder is submerged in an ethanol-water solution so as to test its release rate. A release curve of 10 mg per 24 hours is observed.

Further, a series of hydrophilic polyurethane polymers described in the Examples under the caption "The Polymer System" are useful as coating materials such as for antifog coating or on diving goggles, automobile glass, mirrors, helmets, motorcycle shields, etc. The same coating materials are useful for friction reducing coating for pipes used in irrigation and fire fighting. These coating materials are applied either by spraying or dipping, by using a two package resin and reacting the same in field and applying the same before the reaction is complete or by using a solution in a suitable solvent which solvent may be various ketones, alcohols, various aliphatic and aromatic solvents, various oxygenated solvents, ethers, cycloaliphatic compounds, heterocyclic compounds, etc. The solvent is usually evaporated from the coating by air drying or by forced hot air heating or by other means customarily used in the industry. Additional uses of the polymers as coatings are: in graphic arts, suture and gauze coatings, catheter coatings, blood bag or liner, wound dressing, denture freshener, road coating, building coating, hydrophilic sponges, shower drapes and caps, for flowers and artificial flowers, air filter coatings, and produce coatings, defoliant, spermicide, sterilant, and hormone and steroid carriers.

The above cited uses make use of the unique hydrophilic nature of the coatings. This hydrophilic nature and the ability of the coating to transport vapor, gas, or ions as well as to release chemical species through this coated article makes it an extremely useful polymer carrier.

With respect to the graphic arts, the polymers are useful as gels and substitutes, in photographic emulsions, photo resist, photo engraving, silk screening, art paints, and inks.

As regards noncoating applications, the polymer material may be fabricated from the polymers disclosed above which consists of material suitable for chromatography use, polyblending with other resins, preparation of plastisols, preparation of surgical drapes or blood bags, preparation of chewing gum, surgical gloves, hydrophilic sponges, fibers, contraceptive devices, tablets, pills, tobacco filters, air filters, humidity elements, sensing devices, capillaries, cannulae, toys, entrapments devices, absorbants, artificial leather, gas filters, wet friction rubber soles, etc. Dentures may all be repaired by admixing the polymers of this invention with resins known in the state of dentistry to produce materials that have various degrees of hydrophilicity.

Shapes may be prepared by casting, machining, or thermoforming for industrial, prosthetic or implantable devices. The material in this invention may be prepared by extruding rods or films by injection molding or by blow molding, extrusion of various shapes, casting of films, and other methods are known to those skilled in the engineering of plastic and the present polymers can be readily worked up according to these methods. Material may also be prepared in bulk as granular forms or crumbs for use by industrial plastic fabricators. Materials may also be prepared from these polymers to be used as sprayable powders which are useful in deodorizing. Materials may also be used as spray-on bandages and as bandages applied to a wound consisting of a combination of film and fabric with or without consisting of a combination of film and fabric with or without various agents added. Powders may also be sprayed under arm for deodorizing and antiperspirants with or without antiperspirants such as aluminum chlorhydroxide.

An example of suture coating and/or catheter coating can be carried out by using the polyurethane products of Example 23 and G by placing them into a ketone or alcohol solution at 5 to 20% concentration and dipping said article in solution air drying or forced heat drying followed by subsequent sterilization. One coat or successive coats can be used depending on a film or coating thickness desired, usually 4 to 5 coats are sufficient. In many cases, one coat is adequate. Illustrative prior art embodiments are shown in U.S. Pat. No. 3,566,874; however, the present polymer systems are superior.

Surgical drape materials are also prepared from the solubilized species of the polymers in Examples 19, 23 or G by several methods. One method is to dissolve the polymer in a solvent, e.g., the solvents for the polymer recited herein, and coat this solution onto a release paper and dry in a conventional forced air oven and then coat said film with a pressure sensitive adhesive.

An additional method is to take any of the above described polymer films prepared by blow molding extrusion and coating said film with a pressure sensitive adhesive. Such films have an advantage in that the surgical drape has a very high moisture vapor and transmission rates allowing rapid transportation of perspiration or moisture exuded from the body.

Examples of vessel grafts prepared by extrusion or by casting techniques is the preparation of arteries, veins, or small vessels as either reinforced or nonreinforced tubes; such material is reduced thrombogenicity to the blood, has good elastomeric strength, and allows for equilibration of ions when in contact with blood.

Prosthetic devices may be prepared by casting a shaped device or by injection moulding. Such material may be prepared as knuckle joints, tendons, ligaments, dialytic membranes, heart valves, plastic surgical shapes such as ear lobes, tips of noses, cartilaginous replacements, etc.

Examples of contraceptive devices may be prepared by several methods. One is by polymerizing a shape which includes a steroid or a hormone to result in a shaped device which may be then placed in body cavity, or subcutaneously in the body. These devices can also be prepared by coating presently existing devices with a film containing the same or similar steroids or hormones.

Other uses of the polymer material is as a photographic light sensitive layer used in the manner of the Hydron type material and as disclosed in U.S. Pat. No. 3,620,751, which patent is incorporated by reference herein. Other coating applications of these polymers are disclosed in U.S. Pat. Nos. 3,488,215; 3,635,756; 3,566,874; and 3,669,691. These patents disclose the various uses to which the coating aspect of the polymer system disclosed herein can be utilized and these disclosures again are incorporated by reference.

Other uses of the present polymer system previously only briefly mentioned are water swelling caulking compounds. The polymer resins disclosed herein are admixed with fillers such as powders and pigments, e.g., titanium dioxide, iron oxides, etc. and then reacted with the isocyanate in the field. A two package system may be used and the mixture applied such as by extrusion through a nozzle. Alternatively, the catalyst for the isocyanate reaction may be admixed in the field to the mixture of resin and isocyanates. These water swelling caulking compounds are especially suitable for marine use and waterproofing. Similar applications of the polymer are as swellable fabrics when a base fabric is appropriately coated with the polymers of this invention. Similarly, the present polymers are good wet friction elastomers for applications such as road surface coatings, coatings or shapes for soles, dentures, etc. As artificial leather, the polymer material is useful as a coating or as a higher vapor transmission film suitably reinforced with dispersed fibers and cast in sheet form.

As an outstanding advantage of the present polymer system as a carrier, coating, sheet, or film, etc., its compatability with primer coatings or layers of polyurethane polymers. Various polyurethane polymers of different degrees of water absorbtivity as taught above may be used to obtain a tightly adhering primer coat which may consist of various layers with increasing (or decreasing) water absorbtivity. Consequently, the swelling of the most water swellable layer will not cause delamination failure between coatings or layers as a tailored degree of expansion and contraction with be accommodated by the swelling or contraction characteristics designed into each layer. Thus, extremely hard coating of polyurethane base varnish of outstanding characteristics known in the art may be progressively overcoated with progressively more water absorbent layers of hydrophilic polymers and ultimately with a tenaciously adhering hydrogel without affecting the substrate and yet preserving the same with essentially a hydrogel coating.

Other and further embodiments of the invention are readily apparent from the thorough description of the invention and these embodiments are within the scope of the invention disclosed herein.

What is claimed is:

1. A carrier system comprising an active agent and a hydrophilic polymer as a carrier vehicle therefor, said carrier vehicle comprising a crosslinked polyurethane polymer consisting essentially of
   A. as a resin precursor of said polyurethane polymer, a polyfunctional resin having an equivalent weight of more than 170 and up to 2000 and a numerical carbon to oxygen or carbon to nitrogen ratio of up to 2.5:1 to 1.2:1 or a numerical carbon to ionic group ratio in said resin of 20:1 to 6:1, said resin being selected from the class consisting of:
   1. an adduct of
      a. a dihydroxy compound with propylene imine, ethylene oxide, propylene oxide, ethylene imine, dioxolane or mixtures of same;
      b. a trihydroxy compound with ethylene oxide, propylene oxide, ethylene imine, propylene imine, dioxolane or mixtures of same;
      c. a tetrahydroxy compound with ethylene oxide, propylene oxide, ethylene imine, propylene imine, dioxolane or mixtures of same;
      d. a polyhydroxy compound of more than 4—OH groups with ethylene oxide, propylene oxide, ethylene imine, propylene imine, dioxolane or mixtures of same;
      e. a hydroxy carboxylic acid or a sugar acid with ethylene oxide, propylene oxide, ethylene imine, propylene imine, dioxolane or mixtures of same;
      f. low molecular weight, hydrolyzed polyvinyl acetate, polyacrylic acid or polymethacrylic acid with ethylene oxide, ethylene imine, dioxolane or mixtures of same;
   2. an adduct of trimellitic acid, orthophosphoric acid, pyromellitic acid, or mellitic acid with ethylene oxide, propylene oxide, ethylene imine, dioxolane or mixtures of same;
   3. an adduct of pyrophosphoric acid with ethylene oxide, propylene oxide, ethylene imine, propylene imine, dioxolane or mixtures of same;
   4. an adduct of ammonia or a polyamino compound with ethylene oxide, propylene oxide, ethylene imine, propylene imine, dioxolane or mixtures of same;
   5. an ammonium or quaternary ammonium salt of said adduct of ammonia or a polyamino compound;
   6. a sulfonated reactive-H group terminated polyester resin of a maleic acid ester, itaconic acid ester, fumaric acid ester, mesoconic acid ester or citraconic acid ester wherein a dihydroxy compound precursor of said ester is a glycol of 2 to 6 carbon atoms;
   7. a reactive-H group terminated polyester amide of a lower alkyl dialkanol amine and a diacid wherein said acid is adipic acid, sebacic acid, azelaic acid, maleic acid, phthalic acid, fumaric acid, itaconic acid, mesoconic acid, citraconic acid, and an ammonium or quaternary ammonium compound of said amine groups;
   8. a reactive-H group terminated linear of slightly branched polyamide wherein the amine precursor of said amide is diethylene triamine, triethylene tetramine, tetraethylene pentamine, a polyloweralkylene imine, and the acid precursor of said amide is adipic, sebacic, maleic, azelaic, phthalic, itaconic, mesoconic, or citraconic, an amine salt or mixtures of same, a hydrammonium quaternary ammonium compound thereof, or an adduct of said amide with ethylene oxide, ethylene glycol, dioxolane or propylene glycol;
   9. a reactive-H group terminated polysulfhydryl resin having in the backbone thereof sulfonium, sulfoxide, or sulfone groups; and
   10. mixtures of above resins;
   B. as a urethane linkage precursor of said polyurethane polymer, an aliphatic, alicyclic-aliphatic, mixed aliphatic-aromatic or an aromatic polyfunctional isocyanate, a nitrile carbonate or mixtures of same of a functionality of 2 or higher in an amount from 0.02 in excess of one equivalent weight of isocynante times its functionality per equivalent weight of resin times its functionality up to equi-equivalent weight of said isocyanate to said resin.

2. The carrier system for an active agent as defined in claim 1 and wherein the crosslinked polyurethane polymer is as defined in claim 1 and wherein the resin is a resin having a carbon to oxygen or amine ratio of 2.5 to 1 to 1.2 to 1 of an equivalent weight of more than 170 and a molecular weight less than 2000.

3. The carrier system for an active agent as defined in claim 1 and wherein the crosslinked polyurethane polymer is as defined in claim 1 and wherein the isocyanate is in an amount from 0.02 to 0.15 in excess of the equimolar ratio in reference to the equimolar amount of said isocyanate.

4. The carrier system for an active agent as defined in claim 1 and wherein the crosslinked polyurethane polymer is as defined in claim 1 and wherein the isocyanante to resin is in an amount from 0.02 to 0.10 in excess of the equimolar ratio in reference to the equimolar amount of said isocyanate to said resin.

5. The carrier system for an active agent as defined in claim 1 and wherein the crosslinked polyurethane polymer as defined in claim 1 and wherein the defined excess ratio of isocyanate to resin is 0.02 to 0.1.

6. The carrier system defined in claim 1 and wherein the same is zero order release system.

7. The carrier system as defined in claim 1 and wherein the same is a leachable carrier system.

8. The carrier system as defined in claim 7 wherein the leachable carrier system is an aqueous medium leachable carrier system.

9. The carrier system as defined in claim 7 and wherein the leachable carrier system is a body fluid leachable carrier system.

10. The carrier system as defined in claim 1 wherein the same is a release system for releasing said active agent in a gaseous medium.

11. The carrier system as defined in claim 10 wherein the gaseous medium is air.

12. The carrier system as defined in claim 1 and wherein the polyurethane polymer contains a reaction site for said active agent.

13. The carrier system as defined in claim 1 and wherein the polyurethane polymer as carrier for said active agent is disposed in a liquid medium.

14. The carrier system as defined in claim 13 and wherein the liquid medium is a body fluid.

15. The carrier system as defined in claim 1 and wherein the polyurethane polymer contains reaction sites disposed in a gaseous medium.

16. The carrier system as defined in claim 15 and wherein the gaseous medium is air.

17. A water absorbent coating comprising a crosslinked polyurethane polymer consisting essentially of
A. as a resin precursor of said polyurethane polymer, a polyfunctional resin having an equivalent weight of more than 170 and up to 2000 and a numerical carbon to oxygen or carbon to nitrogen ratio of up to 2.5:1 to 1.2:1 or a numerical carbon to ionic group ratio in said resin of 20:1 to 6:1, said resin being selected from the class consisting of:
1. an adduct of
   a. a dihydroxy compound with propylene imine, ethylene oxide, propylene oxide, ethylene imine, dioxolane or mixtures of same;
   b. a trihydroxy compound with ethylene oxide, propylene oxide, ethylene imine, propylene imine, dioxolane or mixtures of same;
   c. a tetrahydroxy compound with ethylene oxide, propylene oxide, ethylene imine, propylene imine, dioxolane or mixtures of same;
   d. a polyhydroxy compound of more than 4—OH groups with ethylene oxide, propylene oxide, ethylene imine, propylene imine, dioxolane or mixtures of same;
   e. a hydroxy carboxylic acid or a sugar acid with ethylene oxide, propylene oxide, ethylene imine, propylene imine, dioxolane or mixtures of same;
   f. low molecular weight, hydrolyzed polyvinyl acetate, polyacrylic acid or polymethacrylic acid with ethylene oxide, ethylene imine, dioxolane or mixtures of same;
2. an adduct of trimellitic acid, orthophosphoric acid, pyromellitic acid, or mellitic acid with ethylene oxide, propylene oxide, ethylene imine, dioxolane or mixtures of same;
3. an adduct of pyrophosphoric acid with ethylene oxide, propylene oxide, ethylene imine, propylene imine, dioxolane or mixtures of same;
4. an adduct of ammonia or a polyamino compound with ethylene oxide, propylene oxide, ethylene imine, propylene imine, dioxolane or mixtures of same;
5. an ammonium or quaternary ammonium salt of said adduct of ammonia or a polyamino compound;
6. a sulfonated reactive-H group terminated polyester resin of a maleic acid ester, itaconic acid ester, fumaric acid ester, mesoconic acid ester or citraconic acid ester wherein a dihydroxy compound precursor of said ester is a glycol of 2 to 6 carbon atoms;
7. a reactive-H group terminated polyester amide of a lower alkyl dialkanol amine and a diacid wherein said acid is adipic acid, sebacic acid, azelaic acid, maleic acid, phthalic acid, fumaric acid, itaconic acid, mesoconic acid, citraconic acid, and an ammonium or quaternary ammonium compound of said amine groups;
8. a reactive-H group terminated linear of slightly branched polyamide wherein the amine precursor of said amide is diethylene diamine, triethylene tetramine, tetraethylene pentamine, a polyloweralkylene imine, and the acid precursor of said amide is adipic, sebacic, maleic azelaic, phthalic, itaconic, mesoconic, or citraconic, an amine salt or mixtures of same, a hydroammonium quaternary ammonium compound thereof, or an adduct of said amide with ethylene oxide, ethylene glycol, dioxolane or propylene glycol;
9. a reactive—H group terminated polysulfhydryl resin having in the backbone thereof sulfonium, sulfoxide, or sulfone groups; and
10. mixtures of above resins;
B. as a urethane linkage precursor of said polyurethane polymer, an aliphatic, alicyclic-aliphatic, mixed aliphatic-aromatic or an aromatic polyfunctional isocyanate, a nitrile carbonate or mixtures of same of a functionality of 2 or higher in an amount from 0.02 in excess of one equivalent weight of isocyanate times its functionality per equivalent weight of resin times its functionality up to equiequivalent weight of said isocyanate to said resin.

18. A body implant comprising a crosslinked polyurethane polymer consisting essentially of
A. as a resin precursor of said polyurethane polymer, a polyfunctional resin having an equivalent weight of more than 170 and up to 2000 and a numerical carbon to oxygen or carbon to nitrogen ratio of up to 2.5:1 to 1.2:1 or a numerical carbon to ionic group ratio in said resin of 20:1 to 6:1, said resin being selected from the class consisting of:
1. an adduct of
   a. a dihydroxy compound with propylene imine, ethylene oxide, propylene oxide, ethylene imine, dioxolane or mixtures of same;
   b. a trihydroxy compound with ethylene oxide, propylene oxide, ethylene imine, propylene imine, dioxolane or mixtures of same;
   c. a tetrahydroxy compound with ethylene oxide, propylene oxide, ethylene imine, propylene imine, dioxolane or mixtures of same;
   d. a polyhydroxy compound of more than 4—OH groups with ethylene oxide, propylene oxide, ethylene imine, propylene imine, dioxolane or mixtures of same;
   e. a hydroxy carboxylic acid or a sugar acid with ethylene oxide, propylene oxide, ethylene imine, propylene imine, dioxolane or mixtures of same;
   f. low molecular weight, hydrolyzed polyvinyl acetate, polyacrylic acid or polymethacrylic acid with ethylene oxide, ethylene imine, dioxolane or mixtures of same;
2. an adduct of trimellitic acid, orthophosphoric acid, pyromellitic acid, or mellitic acid with ethylene oxide, propylene oxide,, ethylene imine, dioxolane or mixtures of same;
3. an adduct of pyrophosphoric acid with ethylene oxide, propylene oxide, ethylene imine, propylene imine, dioxolane or mixtures of same;
4. an adduct of ammonia or a polyamino compound with ethylene oxide, propylene oxide, ethylene imine, propylene imine, dioxolane, or mixtures of same;
5. an ammonium or quaternary ammonium salt of said adduct of ammonia or a polyamino compound;
6. a sulfonated reactive-H group terminated polyester resin of a maleic acid ester, itaconic acid ester, fumaric acid ester, mesoconic acid ester or citraconic acid ester wherein a dihydroxy compound precursor of said ester is a glycol of 2 to 6 carbon atoms;
7. a reactive-H group terminated polyester amide of a lower alkyl dialkanol amine and a diacid wherein said acid is adipic acid, sebacic acid, azelaic acid, maleic acid, phthalic acid, fumaric acid, itaconic acid, mesoconic acid, citraconic acid, and an ammonium or quaternary ammonium compound of said amine groups;
8. a reactive-H group terminated linear of slightly branched polyamide wherein the amine precursor of said amide is diethylene triamine, thriethylene tetramine, tetraethylene pentamine, a polyloweralkylene imine, and the acid precursor of said amide is adipic, sebacic, maleic azelaic, phthalic, itaconic, mesoconic, or citraconic, an amine salt or mixtures of same, a hydrammonium quaternary ammonium compound thereof or an adduct of said amide with ethylene oxide, ethylene glycol, dioxolane or propylene glycol;
9. a reactive-H group terminated polysulfhydryl resin having in the backbone thereof sulfonium, sulfoxide, or sulfone groups; and
10. mixtures of above resins;

B. as a urethane linkage precursor of said polyurethane polymer, and aliphatic, alicyclic-aliphatic, mixed aliphatic-aromatic or an aromatic polyfunctional isocyanate, a nitrile carbonate or mixtures of same of a functionality of 2 or higher in an amount from 0.02 in excess of one equivalent weight of isocyanate times its functionality per equivalent weight of resin times its functionality up to equiequivalent weight of said isocyanate to said resin.

19. A wet friction elastomer comprising a crosslinked polyurethane polymer consisting essentially of
A. as a resin precursor of said polyurethane polymer, a polyfunctional resin having an equivalent weight of more than 170 and up to 2000 and a numerical carbon to oxygen or carbon to nitrogen ratio of up to 2.5:1 to 1.2:1 or a numerical carbon to ionic group ratio is said resin of 20:1 to 6:1, said resin being selected from the class consisting of:
1. an adduct of
   a. a dihydroxy compound with propylene imine, ethylene oxide, propylene oxide, ethylene imine, dioxolane or mixtures of same;
   b. a trihydroxy compound with ethylene oxide, propylene oxide, ethylene imine, propylene imine, dioxolane or mixtures of same;
   c. a tetrahydroxy compound with ethylene oxide, propylene oxide, ethylene imine, propylene imine, dioxolane or mixtures of same;
   d. a polyhydroxy compound of more than 4—OH groups with ethylene oxide, propylene oxide, ethylene imine, propylene imine, dioxolane or mixtures of same;
   e. a hydroxy carboxylic acid or a sugar acid with ethylene oxide, propylene oxide, ethylene imine, propylene imine, dioxolane or mixtures of same;
   f. low molecular weight, hydrolyzed polyvinyl acetate, polyacrylic acid or polymethacrylic acid with ethylene oxide, ethylene imine, dioxolane or mixtures of same;
2. an adduct of trimellitic acid, orthophosphoric acid, pyromellitic acid, or mellitic acid with ethylene oxide, propylene oxide, ethylene imine, dioxalane or mixtures of same;
3. an adduct of pyrophosphoric acid with ethylene oxide, propylene oxide, ethylene imine, propylene imine, dioxolane or mixtures of same;
4. an adduct of ammonia or a polyamino compound with ethylene oxide, propylene oxide, ethylene imine, propylene imine, dioxolane or mixtures of same;
5. an ammonium or quaternary ammonium salt of said adduct of ammonia or a polyamino compound;
6. a sulfonated reactive—H group terminated polyester resin of a maleic acid ester, itaconic acid ester, fumaric acid ester, mesoconic acid ester or citraconic acid ester wherein a dihydroxy compound precursor of said ester is a glycol of 2 to 6 carbon atoms;
7. a reactive—H group terminated polyester amide of a lower alkyl dialkanol amine and a diacid wherein said acid is adipic acid, sebacic acid, azelaic acid, maleic acid, phthalic acid, fumaric acid, itaconic acid, mesoconic acid, citraconic acid, and an ammonium or quaternary ammonium compound of said amine groups;

8. a reactive—H group terminated linear of slightly branched polyamide wherein the amine precursor of said amide is diethylene triamine, triethylene tetramine, tetraethylene pentamine, a polyloweralkylene imine, and the acid precursor of said amide is adipic, sebacic, maleic azelaic, phthalic, itaconic, mesoconic, or citraconic, an amine salt or mixtures of same, a hydrammonium quaternary ammonium compound thereof, or an adduct of said amide with ethylene oxide, ethylene glycol, dioxolane or propylene glycol;

9. a reactive—H group terminated polysulfhydryl resin having in the backbone thereof sulfonium, sulfoxide, or sulfone groups; and 10. mixtures of above resins;

B. as a urethane linkage precursor of said polyurethane polymer, an aliphatic, alicyclic-aliphatic, mixed aliphatic-aromatic or an aromatic polyfunctional isocyanate, a nitrile carbonate or mixtures of same of a functionality of 2 or higher in an amount from 0.05 in excess of one equivalent weight of isocyanate times its functionality per equivalent weight of resin times its functionality up to equivalent weight of said isocyanate to said resin.

20. The carrier system as defined in claim 1 and wherein the polyurethane polymer is a solution of polymer in dimethylformamide, dioxane or butyrolactone.

21. In a method for releasing an active agent in a medium in which said active agent is used improvement comprising:

incorporating said active agent in a polyurethane polymer as defined in claim 1;

exposing said polyurethane with said active agent to said medium; and releasing said active agent into said medium at a predetermined rate.

22. The carrier system as defined in claim 1 and wherein the active agent is a therapeutically or biologically active agent.

23. The coating as defined in claim 17 and wherein the same is applied in its noncrosslinked state and curing is effected subsequently.

* * * * *